United States Patent [19]
Han et al.

[11] Patent Number: 6,057,093
[45] Date of Patent: May 2, 2000

[54] METHODS AND COMPOSITIONS FOR CONTROLLING TRANSLATION OF HCV PROTEINS

[75] Inventors: Jang H. Han, Lafayette; Richard R. Spaete, Belmont; Byoung J. Yoo; Byung S. Suh, both of Lafayette; Mark J. Selby, San Francisco; Michael Houghton, Danville, all of Calif.

[73] Assignee: Chiron Corporation, Emeryville, Calif.

[21] Appl. No.: 08/439,996

[22] Filed: May 12, 1995

Related U.S. Application Data

[60] Division of application No. 08/128,583, Sep. 28, 1993, abandoned, which is a continuation-in-part of application No. 07/952,799, Sep. 28, 1992, abandoned.

[51] Int. Cl.⁷ .............................. C12Q 1/70; C12Q 1/68; C12N 15/67
[52] U.S. Cl. .................................. 435/5; 435/6; 435/69.1; 536/24.1
[58] Field of Search .............................. 435/320.1, 172.3, 435/69.1, 70.1, 236, 238, 375, 5, 6; 536/24.1, 24.3, 24.31, 24.33, 24.5

[56] References Cited

U.S. PATENT DOCUMENTS

| | | | |
|---|---|---|---|
| 4,593,002 | 6/1986 | Dulbecco | 435/91.41 |
| 5,350,671 | 9/1994 | Houghton | 435/5 |

FOREIGN PATENT DOCUMENTS

| | | |
|---|---|---|
| 0 318 216 | 5/1989 | European Pat. Off. . |
| 0 388 232 | 9/1990 | European Pat. Off. . |
| 0 699 751 | 3/1996 | European Pat. Off. . |
| WO 88/07544 | 10/1988 | WIPO . |
| WO 90/14436 | 11/1990 | WIPO . |
| WO 91/07092 | 5/1991 | WIPO . |
| WO 91/16331 | 10/1991 | WIPO . |

OTHER PUBLICATIONS

Buck et al., "Phosphate–methylated DNA aimed at HIV–1 RNA loops and integrated DNA inhibits viral infectivity," *Science*, 1990, 248, 208–212.

Choo et al, "Genetic organization and diversity of the hepatitis C virus," *Proc. Natl. Acad. Sci., (USA)*, 1991, 88, 2451–2455.

Choo et al., "Isolation of a cDNA Clone Derived from a Blood–Borne Non–A, Non–B Viral Hepatitis Genome," *Science*, 1989, 244, 359–362.

Dienstag, J.L., and Alter, H.J., "Non–A, non–B hepatitis: evolving epidemiologic and clinical perspective," *Seminars in Liver Disease*, 1986, 6, 67–81.

Edery et al., "Activation of double–stranded RNA–dependent kinase (dsI) by the TAR region of HIV–1 mRNA: a novel tranlational control mechanism," *Cell*, 1989, 56, 303–312.

Elroy–Stein et al., Cap–dependent translation of mRNA conferred by encephalomyocarditis virus 5' sequence improves the performance of vaccinia virus/bacteriophage T7 hybrid expression system, *Proc. Natl. Acad. Sci. (USA)*, 1989, 86, 6126–6130.

Federova et al., "The influence of the target structure on the efficiency of alkylation of single–stranded DNA with the reactive derivatives of antisense oligonucleotides," *FEBS*, 1992, 302, 47–50.

Graessman et al., "Inhibition of SV40 gene expression by microinjected small antisense RNA and DNA molecules," *Nucl. Acid Research*, 1991, 19, 53–59.

Han et al., "Characterization of terminal regions of hepatitis C viral RNA: Identification of conserved sequences in the 5' untranslated region and poly(A) tails at the 3' end," *Proc. Natl. Acad. Sci. (USA)*, 1991, 88, 1711–1715.

Houghton et al., "Molecular biology of the hepatitis C viruses: implications for diagnosis, development and control of viral disease," *Hepatology*, 1991, 14, 381–388.

Hu et al., Slot hybridization to detect circulating HCV RNA using a cDNA probe from the 5' non–coding region of the HCV genome, Third International Symposium on HCV (Program and Abstracts) Strasbourg, France, 1991.

Inchauspe et al., "Genomic structure of the human prototype strain H of hepatitis C virus: comparison with American and Japanese isolates," *Proc. Natl. Acad. Sci. (USA)*, 1991, 88, 10292–10296.

Jang et al., "Initiation of protein synthesis by internal entry of ribosomes into the 5' nontranslated region of Encephalomyocarditis virus RNA In vivo," *J. Virol.*, 1989, 63, 1651–1660.

Jobling and Gehrke, "Enhanced translation of chimaeric messenger RNAs containing a plant viral untranslated leader sequence," *Nature*, 1987, 325, 622–625.

Kato et al., "Molecular cloning of the human hepatitis C virus genome from Japanese patients with non–A, non–B hepatitis," *Proc. Natl. Acad. Sci. (USA)*, 1990, 87, 9524–9528.

Kozak et al., "Comparison of initiation of protein synthesis in prokaryotes, eukaryotes, and organells," *Microbiol. Rev.*, 1983, 47, 1–45.

Kozak et al.," Influences of mRNA secondary structure on initiation by eukarotic ribosomes," *Proc.Natl. Acad. Sci. (USA)*, 1986, 83,2850–2854.

Kozak et al., "The scanning model for translation: An update," *J. Cell Biol.*, 1989, 108, 229–241.

Macejak, D.G. and Sarnow, P., "Internal initiation of translation mediated by the 5' leader of a celular mRNA," *Nature*, 1991, 353, 90–94.

(List continued on next page.)

*Primary Examiner*—David Guzo
*Attorney, Agent, or Firm*—Mark J. Rosen; Alisa A. Harbin; Robert P. Blackburn

[57] ABSTRACT

Embodiments of the present invention feature methods and compositions for controlling the translation of viral peptides and proteins from viral nucleic acid, with particular applications to pestivirus and HCV. The methods and compositions feature control elements of the 5'UT region of the viral genome.

1 Claim, 4 Drawing Sheets

OTHER PUBLICATIONS

Okamoto et al., "Nucleotide Sequence of the genomic RNA of hepatitis C virus isolated from a human carrier: comparison with reported isolates for conserved and divergent regions," *J. Gen. Virol.*, 1991, 72, 2697–2704.

Pelletier, J. and Sonenberg N., "Internal initiation of translation of eukaryotic mRNA directed by a sequence derived from poliovirus RNA," *Nature*, 1988, 334, 320–325.

Shyamala, V. and Ames, G.F., "Use of exonuclease for rapid polymerase chain reaciton based In vitro mutagenesis," *Gene*, 1991, 97, 1–6.

Shyamala, V. et al., "Genome walking by single–specific rimer polymerase chain reaction: SSP–PCR," *Gene*, 1989, 84, 1–8.

Shyamalia et al., "Tranlational Control by the 5' Untranslated Region of HCV RNA," Third International Symposium on HCV (Program and Abstracts) Strasbourg France, 1991.

Straus, E. and Strauss, J.H., "Structure and Replication of the Alphavirus Genome," in *The Togaviridae and Flaviviridae*, S. Schleslinger and M.J. Schlesinger (Eds.), Plenum, NY, 1986, 35–90.

Takamizawa et al., "Structure and organization of the hepatitis C virus genome isolted from human carriers," *J. Virol.*, 1991, 65, 1105–1113.

Weiner et al., "Detection of hepatitis C viral sequences in non–A, non–B hepatitis," *Lancet*, 1990, 355(8680), 1–3.

Adam et al., "Internal initiation of translation in retroviral vectors carrying picornavirus 5' nontranslated regions," *J. Virol.*, 1991, 65(9), 4985–4990.

Blight et al., "Detection of hepatitis C virus RNA by in situ hybridization", *Liver*, 1992, 12(4 pt. 2), 286–289.

Chen et al., "Supercoil sequencing: a fast and simple method for sequencing plasmid DNA," *DNA*, 1985, 4(2), 165–170.

Chen et al., "The Taiwanese Hepatitis C Virus Genome: Sequence Determination and Mapping the 5' Termini of Viral Genomic and Anitgenomic RNA," *Virology*, 1992, 188(1), 102–113.

Egholm et al., "Peptide Nucleic Acids (PNA). Oligonucleotide Analogues with and Achiral Peptide Backbone",*JACS*, 1992, 114, 1895–1897.

Eibl et al., "Electrostatic Interactions at Charged Lipid Membrances. Hydrogen Bonds in Lipid Membrane Surfaces", *Biophys. Chem.*, 1979, 10, 261–271.

Felgner et al., "Lipofection: A highly efficient, lipid–mediated DNA–transfection procedure," *Proc. Natl. Acad. Sci.*, 1987, 84, 7413–7417.

Gorman et al., "Recombinant genomes which express chloramphenicol acetyltransferase in mammalian cells," *Mol. Cell Biol.*, 1982, 2(9), 1044–1051.

Han et al., "Selective expression of rat pancreatic genes during embryonic development," *Proc. Natl. Acad. Sci. USA*, 1986, 83, 110–114.

Kato et al., "Distribution of Plural HCV Types in Japan", *Biochem. Biophys. Res. Commun.*, 1991, 18(1), 279–285.

Lamas et al., "Detection of hepatitis C virus (HCV) RNA sequences in liver tissue by in situ hybridization",*J. Hepatology*, 1992, 16(1–2), 219–223.

Laemmli, "Cleavage of structural proteins during the assembly of the head of bacteriophage T4," *Nature*, 1970, 227, 680–685.

Letsinger et al., "Cholesteryl–conjugated oligonucleotides: Synthesis, properties, and activity as inhibitors of replication of human immunodeficiency virus in cell culture", *Pro. Natl. Acad. Sci. (USA)*, 1989, 86, 6553–6556.

Li et al., "Evidence of two major genotypes of hepatitis C virus in France and close related of the predominant one with the prototype virus", *J. Hepatology*, 1991, 13(4), S33–S37.

Miller, "Assay of Beta–Galactosidase" in *Experiments in Molecular Genetics*, Cold Spring Laboratory, Cold Spring Harbour, NY, 1972, 352–355.

Mukhopadhyay et al., "Specific Inhibition of K–ras Expression and Tumorigenicity of Lung Cancer Cells by Antisense RNA," *Cancer Res.*, 1991, 51, 1744–1748.

Muller et al., "Peripheral blood leukocytes serve as a possible extrahepatic site for hepatitis C virus replication", *J. Gen. Virol.*, 1993, 74(pt. 4), 669–676.

Nielson, et al., "Sequence–Selective Recognition of DNA by Strand Displacement with a Thymine–Substituted Polyamide", *Science*, 1991, 254, 1497–1500.

Nouri et al., "Detection of Genomic and Intermediate Replicative Strands of Hepatitis C Virus in Liver Tissue by In Situ Hybridization", *J. Clinical Investigation*, 1993, 91(5), 2226–2234.

Okamoto et al., "Typing hepatitis C virus by polymerase chain reaction with type–specific primers: application to clinical surveys and tracing infectious sources", *J. Gen. Virol.*, 1992, 73(pt. 3), 673–679.

Saiki et al., "Primer directed enzymatic amplification of DNA with a thermostable DNA polymerase," *Science*, 1988, 239(4839), 487–491.

Schleiss et al., "Translational control of humancytomegalovirus gp48 expression," *J. Virol.*, 1991, 65(12), 6782–6789.

Shyamala et al., "Use of exonuclease for rapid polymerease chain reaction based in vitro mutagenesis," *Gene*, 1991, 197, 1–6.

Soneneberg, "Cap–binding protein of eukaryotic mRNA: functions in initiation and control of translation," *Prog. Nucleic Acid Res. Molec. Biol.*, 1988, 35, 173–207.

Stamatatos et al., "Interactions of Cationic Lipid Vesicles with Negatively Charged Phospholipid Vesicles and Biological Membranes", *Biochem.*, 1988, 27, 3917–3025.

Tsukiyama–Kohara et al., "Internal ribosome entry site within hepatitis C virus RNA," *J. Virol.*, 1992, 66(33), 1476–1483.

Tsukiyama–Kohara et al., "Antigenicities of Group I and II Hepatitus C Virus Polypeptides—Molecular Basis of Diagnosis", *Virology*, 1993, 192(2), 430–437.

Yamada et al., "Localization of Hepatitis C Viral RNA and Capsid Protein in Human Liver", *Digestive Diseases and Science*, 1993, 38(5), 882–887.

Yoo et al., "5' End–Dependent Translation Initiation of Hepatitis C Viral RNA and the Presence of Putative Positive and Negative Translational Control Elements within the 5' Untranslated Region", *Virology*, 1992, 191(2), 889–899.

Zhang et al., "Antisense Oligonucleotide Inhibition of Hepatitis C Virus (HCV) Gene Expression in Livers of Mice Infected with an HCV–Vaccinia Virus Recombinant", *Antimicrobial Agents Chemotherapy*, 1999, 43(2), 347–353.

Letter from G. Reeck et al. Cell 50:667 Aug. 28, 1987.

W. James et al. Antivir. Chem. & Chemother. 2(4)191–214 (1991).

E. Uhlmann et al. Chem. Rev. 90(4) 543–584 (1990).

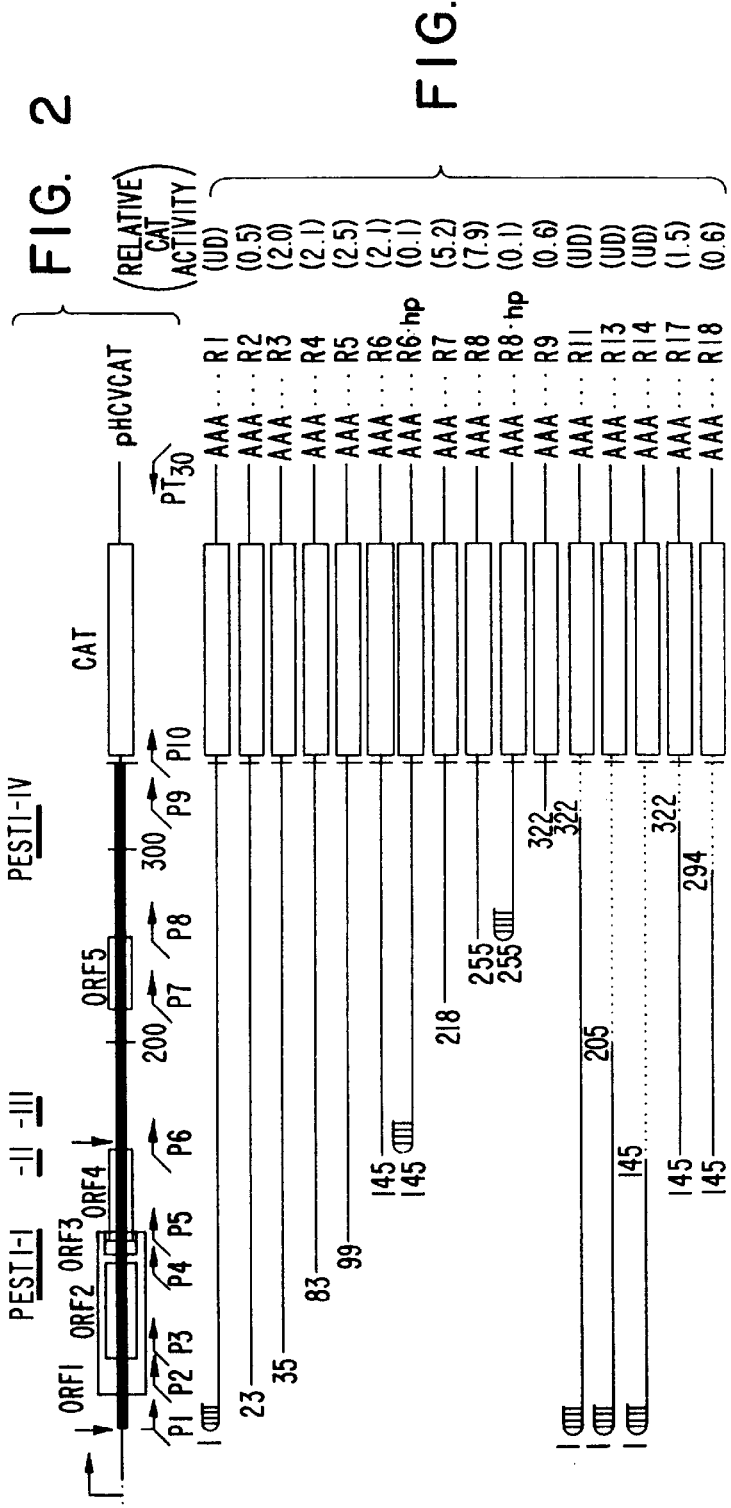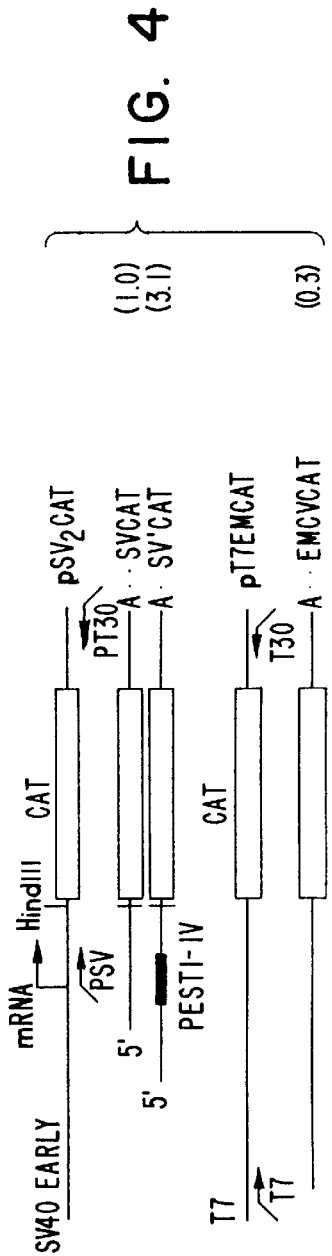
FIG. 2
FIG. 3
FIG. 4

METHODS AND COMPOSITIONS FOR CONTROLLING TRANSLATION OF HCV PROTEINS

CROSS-REFERENCE TO RELATED APPLICATION

This application is a divisional of application Ser. No. 08/128,583, filed Sep. 28, 1993, now abandoned, which is a continuation-in-part of U.S. application Ser. No. 07/952,799, filed on Sep. 28, 1992, now abandoned.

TECHNICAL FIELD

The invention relates to compositions and methods for controlling the translation of hepatitis C virus (HCV) proteins. HCV has been referred to as blood-borne non-A, non-B hepatitis virus (NANBV) infection. More specifically, embodiments of the present invention feature compositions and methods for the control and regulation of HCV translation in vivo. The compositions and methods have applications for decreasing or increasing HCV replication, and decreasing or increasing the expression of HCV proteins.

BACKGROUND OF THE INVENTION

The prototype isolate of HCV was characterized in U.S. patent application Ser. No. 122,714, abandoned (See also EPO Publication Nos. 318,216; 388,232). As used herein, the term "HCV" includes new groups, genotypes and isolates of the same viral species. The term "HCV-1" is used in the same sense as in EPO Publication No. 318,216.

HCV is a transmissible disease distinguishable from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). HCV was first identified in blood-transfused individuals. Post-transfusion hepatitis (PTH) occurs in approximately 10% of transfused patients, and HCV accounts for up to 90% of these cases. The disease frequently progresses to chronic liver damage (25–55%).

There presently exists a great need to control the translation process with respect to viral nucleic acids. Control of the translation process may constitute an effective therapy for viral disease. By way of example, without limitation, the ability to decrease the expression of viral proteins may limit the disease. The ability to increase the expression of viral proteins in vivo may give rise to strong immune stimulation. The ability to increase the expression of viral proteins may also produce greater amounts of viral proteins which can be more readily purified.

The HCV genome is comprised of a single positive strand of RNA. A schematic representation of the HCV genome is depicted in FIG. 1. The HCV genome possesses a continuous, translational open reading frame (ORF) that encodes a polyprotein of about 3,000 amino acids. In the ORF, the structural protein(s) appear to be encoded in approximately the first quarter of the N-terminal region, with the remainder of the polyprotein responsible for encoding non-structural proteins.

The HCV genome has an area at the 5' end which is not known to translate any proteins or polypeptides. The region is referred to as the 5' untranslated region (5'UT region or 5' UTR) or the 5' leader region.

The 5'UT region contains up to five upstream ORFs, the first four of which are overlapping in HCV-1, the prototype HCV isolate (Choo et al., "Genetic organization and diversity of the hepatitis C virus," Proc. Natl. Acad. Sci. USA (1991) 88:2451–2455; Han et al., "Characterization of terminal regions of hepatitis C viral RNA: Identification of conserved sequences in the 5' untranslated region and poly (A) tails at the 3' end," Proc. Natl. Acad. Sci. (USA) (1991) 88:1711–1715). The 5'UT region is homologous in nucleotide sequence to pestiviruses (Han et al.).

Primer extension analysis has revealed that two prominent species of HCV RNA exist in samples derived from infected patients Man et al.). One of the species is longer, and is presumed to be full-length genomic RNA. The longer, full-length genomic RNA has a 5' terminus which is predicted to form a hairpin structure (Han et al.; Inchauspe et al., Abstract, Third International Symposium on HCV, V. 19, Strasbourg, France, 1991; Okamoto et al., "Nucleotide sequence of the genomic RNA of hepatitis C virus isolated from a human carrier: Comparison with reported isolates for conserved and divergent regions," J. Gen Virol. (1991) 72:2697–2704). The remaining species is shorter, presumably a 5' subgenomic RNA, the 5' terminus of which starts 145 nucleotides from the 5' terminus of the longer RNA Han et al.).

Antisense polynucleotide molecules for HCV are generally disclosed in EP Publication No. 388,232.

BRIEF DESCRIPTION OF THE INVENTION

The present invention features compositions and methods for controlling the translation of HCV proteins from HCV nucleic acid. The invention is based on the utilization of nucleic acids complementary to a small region from the 5' end of HCV RNA. One embodiment of the present invention features a method of controlling the translation of HCV proteins from HCV nucleic acid comprising the step of contacting a non-naturally occurring first nucleic acid with HCV nucleic acid under hybridizing conditions. The first nucleic acid is an antisense nucleic acid: it has a sequence substantially complementary to a sequence of the sense strand within the 5'UT region of HCV nucleic acid. The sense strand is the strand of genomic or messenger RNA which is subjected to the translation process. The first nucleic acid is placed with the HCV nucleic acid under conditions where the two nucleic acids are capable of forming a hybridization product which hybridization product alters the level of translation of the HCV nucleic acid.

The present method can be performed within a subject infected with HCV. The method may also be used within cells to generate viral proteins of interest in vitro. The method may be used as a therapy for HCV infections.

Accordingly, in one aspect of the invention, a method of controlling the translation of hepatitis C virus (HCV) proteins from HCV nucleic acid is provided comprising the steps of: (a) providing a non-naturally occurring first nucleic acid which first nucleic acid comprises a sequence complementary to a sense strand within the 5'UT region of HCV nucleic acid; and (b) contacting said HCV nucleic acid with said first nucleic acid under conditions where said first nucleic acid and HCV nucleic acid are capable of forming a hybridization product, said hybridization product altering the level of translation of said HCV nucleic acid.

In another aspect of this invention, a composition for controlling the translation of HCV proteins from HCV nucleic acid is provided, the composition comprising a first nucleic acid or means for making a first nucleic acid having a sequence complementary to a sequence of the sense strand within the 5'UT region of HCV nucleic acid. Preferably, the sequence of the first nucleic acid is complementary to a sequence selected from within (SEQ ID NO: 1).

In a further aspect of this invention, a method of controlling HCV is provided including the steps of: (a) generating a first nucleic acid as a transcription product of a second nucleic acid operably linked to a promoter; (b) placing the second nucleic acid and promoter in a cell infected with HCV, which cell is capable of transcribing the second nucleic acid to produce the first nucleic acid. The method can also be employed to prevent the expression of HCV proteins in cells which are not infected with HCV but may be subjected to infection at some time in the future ("susceptible" cells).

In yet another aspect of the invention, a method of controlling the translation of HCV proteins through the nucleotides of the 5'UT hairpin is provided, the method comprising the steps of placing and holding the hairpin sequences in one of two positions, wherein at least one of said positions is the hairpin configuration.

In a still further aspect of the invention, a kit for the treatment and control of HCV infections is provided, the kit comprising as an article of manufacture the compositions of the present invention. Preferably, the kit includes instructions for its use, and may optionally contain vectors and other vehicles for placing the nucleic acid into a cell or individual.

In another aspect of the invention, a method of enhancing the translation of a first nucleic acid is provided, the method comprising the step of operably linking the first nucleic acid with a second non-naturally occurring nucleic acid having a sequence corresponding to sequences within the pestivirus homology box IV of HCV. A composition for enhancing the translation of a first nucleic acid is also provided, the composition comprising a non-naturally occurring second nucleic acid having sequences corresponding to sequences within the pestivirus homology box IV of HCV, which sequences are capable of being operably linked to the first nucleic acid.

BRIEF DESCRIPTION OF THE DRAWINGS

FIG. 2 is a schematic representation of the HCV viral RNA genome, which viral RNA genome is modified to include MlRNA sequences for chloramphenicol acetyl transferase (CAT);

FIG. 3 is a schematic representation of the modified HCV viral RNA genome with further deletions and modifications;

FIG. 4 is a schematic representation of five RNA constructs, pSV$_2$, CAT, SVCAT, SVACAT, pT7EMCAT, and EMCVCAT;

DETAILES DESCRIPTION OF THE INVENTION

Figure 1:
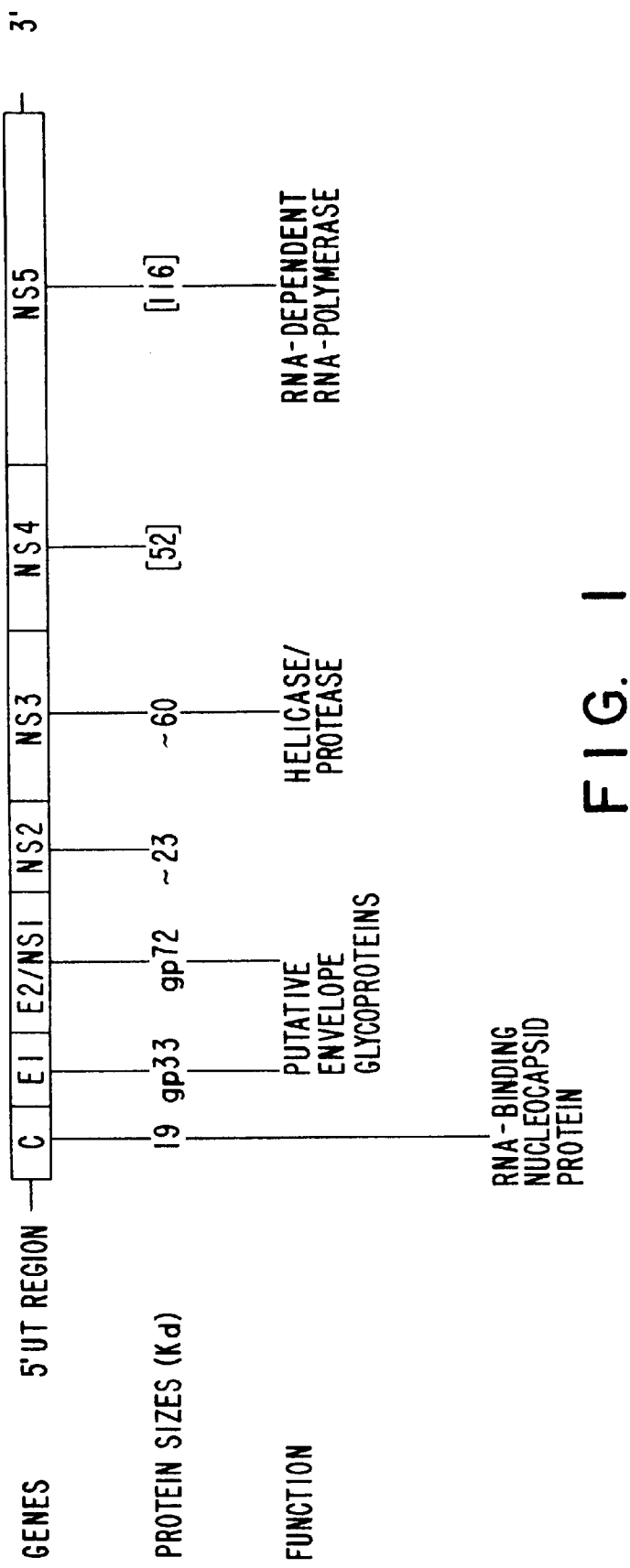
FIG. 1 is a schematic representation of the HCV viral genome.

The present invention will be described in detail as methods and compositions for controlling the translation of HCV nucleic acid. The compositions and methods will be discussed in detail with respect to HCV nucleic acid. However, the description with resect to HCV nucleic acid is not intended to limit the invention to HCV, which is used solely to exemplifr features of the invention.

The practice of the present invention will employ, unless otherwise indicated, conventional techniques of chemistry, molecular biology, microbiology, recombinant DNA, and immunology, which are within the skill of the art. Such techniques are explained fully in the literature. See e.g., Sambrook, Fitsch & Maniatis, Molecular Cloning; *A Laboratory Manual* (1989); DNA Cloning, Volumes I and II (D. N Glover ed. 1985); Oligonucleotide Synthesis (M. J. Gait ed, 1984); Nucleic Acid Hybridization (B. D. Hames & S. J. Higgins eds. 1984); the series, Methods in Enzymology (Academic Press, Inc.), particularly Vol. 154 and Vol. 155 (Wu and Grossman, eds.).

Definitions:

Definitions for selected terms used in the application are set forth below to facilitate an understanding of the invention. The term "corresponding" means homologous to or complementary to a particular sequence of nucleic acid. As between nucleic acids and peptides, corresponding refers to amino acids of a peptide in an order derived from the sequence of a nucleic acid or its complement.

The term "non-naturally occurring nucleic acid" refers to a portion of genomic nucleic acid, cDNA, semisynthetic nucleic acid, or synthetic origin nucleic acid which, by virtue of its origin or manipulation: (1) is not associated with all of a nucleic acid with which it is associated in nature, (2) is linked to a nucleic acid or other chemical agent other than that to which it is linked in nature, or (3) does not occur in nature.

As used herein, the terms "polynucleotide", "oligonucleotide" and "nucleic acid" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing non-nucleotidic backbones (e.g., protein nucleic acids and synthetic sequence-specific nucleic acid polymers commercially available from the Anti-Gene Development Group, Corvallis, Oreg., as Neugene™ polymers) or nonstandard linkages, providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside", "nucleotide" and "nucleic acid" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

Organization of HCV Genome:

Libraries of cDNA of HCV are derived from nucleic acid sequences present in the plasma of an HCV-infected chimpanzee or human. The construction of one of these libraries, the "c" library (ATCC No. 40394), is described in PCT Pub. No. WO90/14436. The corresponding DNA sequences relevant to the present invention are set forth herein as (SEQ ID NO: 1).

The 5'UT region is approximately 341 nucleotides long, based on at least five putative full-length HCV clones reported to date (Han et al.; Inchauspe et al.; Okamoto et al.). Unlike the polyprotein region, the 5'UT region of HCV isolates are highly conserved. As seen in FIG. 2, the 5'UT region contains up to five upstream ORFs, the first four of which are overlapping in HCV-1, the prototype HCV isolate (Choo et al.; Han et al.). The 5'UT region is substantially homologous in nucleotide sequence to pestiviruses (Han et al.). Thus, the discussion regarding the regulation of translation of HCV nucleic acid is applicable to other pestiviruses.

Primer extension analysis has revealed two prominent species of HCV RNA (Han et al.). One species is longer and presumed to be full-length genomic RNA. The 5' terminus of the longer, full-length genomic RNA is predicted to form a hairpin structure (Han et al.; Inchatispe et al.; Okamoto et al.). The 5' terminus of the shorter 5' subgenomic RNA starts 145 nucleotides from the 5' terminus of the longer RNA (Han et al.).

Nucleic Acids:

Embodiments of the present invention feature nucleic acids that can interact with distinct cis-acting control elements of HCV and therefore can block, repress or enhance translation of HCV nucleic acid.

One embodiment of the present invention features a method of controlling the translation of HCV proteins from HCV nucleic acid comprismg the step of placing a non-naturally occurring first nucleic acid with HCV nucleic acid. The first nucleic acid has a sequence complementary to a sequence of the sense strand within the 5'UT region of HCV nucleic acid. The first nucleic acid is placed with the HCV nucleic acid under conditions where the first nucleic acid is capable of forming a hybridization product, and altering the level of translation of the HCV nucleic acid.

Preferably, the antisense nucleic acid of this invention is RNA, DNA or a modified nucleic acid. Examples, without limitation, of modified nucleic acids are degradation-resistant sulfurized and thiophosphate derivatives of nucleic acids, and polynucleoside amides (PCT Publication No. WO91/16331 to Stec et al.; PCT Publication No. WO88/07544 to Zon et al.; P. E. Nelsen, et al., *Science* (1991) 254:1497–1500; M. Egholm, *JACS*, (1992) 114:1895–1897). Particularly preferred design modifications of the antisense nucleic acids of this invention are modifications that are designed to: (1) increase the intracellular stability of the nucleic acid; (2) increase the cellular permeability of the nucleic acid; (3) increase the affinity of the nucleic acid for the sense strand, or (4) decrease the toxicity (if any) of the nucleic acid. Many such modifications are known in the art, as described in ANTISENSE RESEARCH AND APPLICATIONS (S. T. Crooke and B. Debleu, eds., CRC Press, 1993). Thus, the nucleic acids may contain altered or modified bases, sugars or linkages, be delivered in specialized systems such as liposomes or by gene therapy, or may have attached moieties. Such attached moieties include hydrophobic moieties such as lipids that enhance interaction with cell membranes, or polycationic moieties such as polylysine that act as charge neutralirs of the phosphate backbone. Particularly preferred lipids that may be attached are cholesterols. The moieties may be attached at the 3' or 5' ends of the nucleic acids, and also may be attached through a base, sugar, or internucleoside linkage.

Other moieties may be capping groups specifically placed at the 3' or 5' ends of the nucleic acids to prevent exonuclease degradation. Such capping groups include, but are not limited to, hydroxyl protecting groups known in the art, including glycols such as polyethylene glycols, tetraethylene glycol and the like.

Preferably, the first nucleic acid has at least 10 nucleotides in a sequence substantially complementary to a sequence of the sense strand within the 5'UT region of HCV. More preferably, the first nucleic acid has at least 12 nucleotides in such complementary sequence; more preferably, fifteen nucleotides; and, more preferably, twenty nucleotides. Preferably, the first nucleic acid has less than 100 nucleotides in such complementary sequence; and more preferably, less than 50 nucleotides. Most preferably, the nucleic acid has approximately 20–30 nucleotides capable of forming a stable hybridization product with a sense sequence of the 5'UT region of HCV.

The 5'UT region of the HCV virus is set forth in (SEQ ID NO: 1). One preferred nucleic acid of this invention is capable of binding approximately 23 nucleotides of the 5' hairpin structure. The 23 nucleotides are in positions 1–23 of (SEQ ID NO: 1). Preferably, the nucleic acid forms a triple helix with the sequences associated with the hairpin, inhibiting its cleavage from the remaining portion of the messenger RNA.

Another preferred nucleic acid of this invention is capable of binding to a 28 nucleotide area known-as pestivirus homology box IV. The pestivirus homology box IV area spans bases 291 to 318 of (SEQ ID NO: 1).

A further preferred nucleic acid of this invention is capable of binding to an area defined by the site at which the long full-length genomic RNA is cleaved to form a shorter, subgenomic RNA. This cleavage area spans an area of approximately 50 nucleotides up and down stream of position 145 of (SEQ ID NO: 1).

Still another preferred nucleic acid is denoted "AS5" capable of binding to a region that overlaps the pestivirus homology box IV spanning bases 277 to 300 of (SEQ ID NO: 1). In a preferred embodiment of this invention, the AS5 nucleic acid is fully phosphorothioated, i.e., only contains phosphorothioate linkages in place of the natural phosphodiester linkages. In another preferred embodiment of this invention, the AS5 nucleic acid is covalently linked to a cholesteryl moiety, more preferably through the 3' end of the nucleoside.

Nucleic Acid Delivery:

The nucleic acid can be placi in the cell through any number of ways known in the art. Cells can be transfected with a second nucleic acid capable of generating the first nucleic acid as a transcription product; e.g., by including the second nucleic acid in a viral carrier as shown in Dulbecco, U.S. Pat. No. 4,593,002; or by gene therapy methods such as including the second nucleic acid in a retroviral vector. One example of antisense gene therapy is described in an article by Mukhopadhyay et al., "Specific Inhibition of K-RAS Expression and Tumorigenicity of Lung Cancer Cells by Antisense RNA," *Cancer Research*, 51:1744–1748 (1991).

The present invention also contemplates vehicles for placing the first nucleic acid or the second nucleic acid into cells infected with HCV, or cells which are to be protected from HCV infection. Examples of such vehicles comprise vectors, liposomes and lipid suspensions, such as N-(1-(2, 3-dioleyloxy)propyl)-N,N,N-trimethylammonium methylsulfate (DOTAP), N-[1-(2,3-dioleyloxy)propyl]-N,N,N-trimethylammonium chloride (DOTMA), and the like. Alternatively, the lipid may be covalently linked directly to the first nucleic acid.

The antisense nucleic acid may also be linked to moieties that increase cellular uptake of the nucleic acid. These moieties may be hydrophobic, such as phospholipids or lipids such as steroids (e.g., cholesterol), or may be polycationic (e.g., polylysine). The hydrophobic or polycationic moieties are attached at any point to the antisense nucleic acid, including the 3' and 5'ends, base, sugar hydroxyls, and internucleoside linkages.

A particularly preferred moiety to increase uptake is a cholesteryl group. Cholesteryl-like groups may be attached through an activated cholesteryl chloroformate, for example, or cholic acid, by means known in the art as reflected in ANTISENSE RESEARCH AND APPLICATIONS, supra. In one example (p. 318) a cholesterol moiety may be conjugated to a 2' hydroxyl group using an aminolinker and a functional group on the cholesterol that reacts with an amine. In another method, a cholesteryl group is linked to the 3' phosphate using $CCl_4$ and cholesteryloxycarbonylaminoethylamine as described in R. L. Letsinger et al., *Proc. Natl. Acad. Sci.* (*USA*) (1989) 86:6553–6556.

Use of the 5' Hairpin:

Enhancement of translation may allow stronger immune responses. Blocking or decreasing translation of viral nucleic acid may decrease the pathology of the viral infection. In one aspect of the invention, a method of controlling the translation of HCV proteins through the nucleotides of the hairpin at nucleotides 1–23 is provided, the method comprising the steps of placing and holding the hairpin sequences in one of two positions, at least one of said positions is the hairpin configuration. In the hairpin configuration, translation of viral nucleic acid in vivo is blocked or substantially decreased. At least one of said positions comprises a non-hairpin linear configuration or complete removal of the nucleotides associated with the hairpin. A linear configuration allows translation of viral nucleic acid. Removal of the hairpin nucleotides enhances the translation of viral nucleic acid. Preferably, the hairpin structure is stabilized by placing a non-naturaly occurring first nucleic acid with HCV nucleic acid under conditions in which the first nucleic acid forms a triple helix with the hairpin structure.

The sequences associated with the hairpin inhibit translation. One embodiment of the present invention features a first nucleic acid having a first sequence capable of forming a hairpin configuration and a second sequence capable of binding to mRNA. Preferably, the first sequences have sequences corresponding to bases 1 to 23 of (SEQ ID NO: 1). Preferably, the second sequences hybridize to the shorter subgenomic RNA.

Pharmaceutical Formulations:

The compositions of the present invention may be prepared for pharmaceutical administration. Injection preparations and suppositories may usually contain 1–10 mg of the nucleic acid or nucleic acid analog per ampoule or capsule. For human patients, the daily dose is about 0.1–1,000 mg, preferably 1–100 mg (from 10–20 mg/kg to 1000–2000 mg/kg body weight). However, the particular dose for each patient depends on a wide range of factors, for example, on the effectiveness of the particular nucleic acid or nucleic acid analog used, on the age, weight, general state of health, sex, on the diet, on the time and mode of administration, on the rate of elimination, combination with other medicaments jointly used and severity of the particular diseases to which the therapy is applied.

Pharmaceutical articles of manufacture, within the scope of the present invention, include articles wherein the active ingredients thereof are contained in an effective amount to achieve its intended purpose. A preferred range has been described above, and determination of the most effective amounts for treatment of each HCV infection is with the skill of the art.

In addition to the nucleic acid and their sulfilrized and phosphorothioated analogs of the present invention, pharmaceutical preparations may contain suitable excipients and auxiliaries which facilitate processing of the active compounds. The preparations, particularly those which can be administered orally and which can be used for the preferred type of administration, such as tablets, dragees, and capsules, and preparations which can be administered rectally, such as suppositories, as well as suitable solutions for administration parenterally or orally, and compositions which may be administered bucally or sublingually, may contain from 0.1 to 99% by weight of active ingredients, together with the excipient. A preferred method of administration is parenteral, especially intravenous administration.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyloleate or triglycerides. Aqueous injection suspensions may contain substances which increase the viscosity of the suspension, for example, sodium carboxymethyl cellulose, sorbitol, and/or dextran. Optionally, the suspension may also contain stabilizers.

Additionally, the compounds of the present invention may also be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as dicetylphosphate, stearylamine, or phosphatidic acid, and/or other materials of a hydrophobic nature. The diameters of the liposomes generally range from about 15 nm to 5 microns. Particularly preferred lipids for the preparation of liposomes and/or lipid suspensions are DOTMA and DOTAP.

DOTAP is commercially available from Boehringer Mannheim, or may be prepared following the methods described by L. Stamatatos et al., *Biochem* 27:3917–25 (1988); H. Eibl et al., *Biophys Chem* 10:261–71 (1979). DOTMA is commercially available under the name Lipofectin* (available from BRL, Gaithersburg, Md.), and is described by P. L. Felgner et al. *Proc Nat Acad Sci USA* 84:7413–17 (1987).

The present invention will now be illustrated by reference to the following examples which set forth particularly advantageous embodiments. However, it should be noted that these embodiments are illustrative and are not to be construed as restricting the invention in any way.

EXAMPLES

I. MATERIALS AND METHODS

A. Cells, bacterial strains and plasmids. HUH7, HeLa and HepG2 cells were grown in Dulbecco's modified Eagle's medium supplemented with 10% bovine calf serum (Gibco-BRL, Gaithersburg, Md.). Cells were grown in the presence of 7% $CO_2$. All plasmids were grown in *Escherichia coli* HB101, purchased from Gibco-BRL.

B. Enzymes. Restriction enzymes and T4 DNA ligase were purchased from Boehringer Mannheim (Indianapolis, Ind.), Taq-polymerase from Perkin Elmer (Norwalk, Conn.), T7 RNA polymerase and RNasin, from Promega (Madison, Wis.).

C. Contruction of expression plasmids. The construction of plasmid pT7EMCAT and $pSV_2CAT$ have been described (Elroy-Stein et al., "Cap-dependent translation of mRNA conferred by encephalomyocarditis virus 5' sequence improves the performance of vaccinia virus/bacteriophage T7 hybrid expression system," *Proc. Natl. Acad. Sci. (USA)* (1989) 86:6126–6130; Gorman et al., "Recombinant genomes which express chloramphenicol acetyltransferase in mammalian cells," *Mol. Cell Biol.* (1989) 2:1044–1051). Plasmid pHCVCAT was constructed by attaching HindIII sites at the both ends of the 5'UT region of HCV cDNA (Han et al.) by PCR (Saiki et al., "Primer-directed enzymatic amplification of DNA with a thermostable DNA polymerase," *Science* (1988) 230:1350–1354) and cloning the resultant fragment into the HindIII site of $pSV_2CAT$.

Plasmid pEQ355 was constructed by inserting the 341 bp 5'UT region of HCV-1 into the HindIII/Asp718 sites resident in the multiple cloning site of beta galactosidase (β gal) expression plasmid, pEQ176 (Schleiss et al., "Translational control of human cytomegalovirus gp48 expression," *J. Virol.* (1991) 65:6782–6789). The HCV-1 5'UT region was generated as a HindIII/Asp718 PCR fragment using B114, an EcoRl fragment from a lambda vector as template.

Plasmid pEQ391 [pCMV(CAT/HCV/LacZ)], was generated by ligating a 716 bp HindIII/BanI fragment encoding the CAT gene isolated from plasmid $pSV_2CAT$ (Gorman et al.) into plasmid pEQ355 at the HindIII site. The HindIII sites were ligated and the BanI site and unligated HindIII site in pEQ355 were blunted with Klenow and religated.

Plasmid pEQ416 [pCMV(CAT/polio/LacZ)], was constructed by ligating a 716 bp HindIII/BamHI CAT gene encoding PCR fragment generated using $pSV_2CAT$ as template, a 995 bp BamHI/XhoI fragment encoding the poliovirus 5' UT region along with β gal expression plasmid pEQ176 digested at the HindIII/XhoI site in the polylinker.

pEQ396 is a β gal expression plasmid constructed by cloning the 5'UT region poliovirus sequence taken from pLNPOZ (Adam et al., "Internal initiation of translation in retroviral vectors carrying picornavirus 5' nontranslated regions," *J. Virol.* (1991) 65:4985–4990) as an XhoI/PstI fragment blunted using Klenow, into pEQ377 digested at XbaI/SnaBI sites in the polylinker. The XbaI site was also filled with Klenow to create blunt ends. Transcription of β gal in pEQ377 is promoted by T7 bacteriophage promoter.

Plasmid p(CAT/SV40/LacZ) was constructed by ligating the 716 bp HindIII/BamHI CAT gene encoding PCR fragment described above, along with SV40 polyadenylation signals and β gal expression plasmid pEQ176 digested with HindIII/BglII. The authenticity of all PCR products was verified by sequencing each of the resulting segments in the plasmids (Chen and Seeburg, "Supercoil sequencing: a fast and simple method for sequencing plasmid DNA," *DNA* (1985) 4:165–170).

D. Construction of hybrid CAT RNAs. Segments of $pSV_2CAT$ vectors were amplified by PCR as described (Saiki et al.; Shyamala and Ames, "Use of exonuclease for rapid polymerase chain reaction based In vitro mutagenesis," *Gene* (1991) 97:1–6). Each segment is depicted in FIGS. 2 and 3. Each sense primer (PSV or P1 to P9) was designed to have a bacteriophage T7 promoter (TAATACGACTCACTATAG) Seq. ID No.3 at the 5' end and a SV40 or HCV sequence of 16 to 18 bases at the 3' end. An antisense primer had a stretch of 40 Ts Seq. ID No.4 at the 5' end and a complementary SV40 sequence (GGAGGAGTAG) Seq. ID No.5 at the 3' end. This sequence binds to vectors, 350 bp after a stop codon in the CAT gene by virtue of a perfect match of 10 nucleotides and an additional poly A track present in the template DNA. A segment of pT7EMCAT was amplified by primers T7 and T30.

Each PCR product was transcribed by T7 polymerase with or without cap analogue (Promega, p2010), treated with DNase, extracted with phenol-chloroform, and precipitated twice with ethanol in the presence of 2.5 M ammonium acetate. Concentration of each poly(A)+ RNA was estimated by UV absorption and confirmed by Northern and dot blot hybridization as described (Han et al., "Selective expression of rat pancreatic genes during embryonic development," *Proc. Natl. Acad. Sci. (USA)* (1986) 83:110–114) using JHC271 as a probe. In SV*CAT, R11, R13 and R14, sequences were internally inserted or deleted by an overlapping PCR method (Shyamala and Ames). The PCR products were confirmed to be correct by sequencing.

E. Translation of hybrid CAT RNAs in vitro. Synthetic RNAs were translated in nuclease-treated rabbit reticulocyte lysate (Gibco-BRL) in the presence of 140 mM potassium acetate, as suggested by the manufacturer. Additional studies examining the influence of $K^+$ion concentration on cap dependence were done in the presence of 50, 100, 150, and 200 mM potassium acetate. Aliquots of the translation product labeled with [$^{35}S$]methionine were analyzed by electrophoresis in a 12% polyacrylamide gel as previously described (Laemmli, "Cleavage of structural proteins during the assembly of the head of bacteriophage T4, " *Nature* (1970) 227:680–685).

F. Transfection of hybrid CAT RNAs into mammalian cells for CAT assay. Two micrograms each of synthetic RNA was transfected into $1\times10^6$ cells in a 3.5 cm Costar plate (Thomas Scientific, Swedesboro, N.J.) using 15 mg of lipofectin (Gibco-BRL) according to the procedure of Felgner et al. "Lipofection: A highly efficient, lipid-mediated DNA-transfection procedure," *Proc. Natl. Acad. Sci. (USA)* (1987) 84:7413–7417, modified by the manufacturer. Cells were incubated overnight and harvested for CAT assay as previously described (Gorman et al.). The relative CAT activity was shown to be linear between 0.5 mg and 5 mg of transfected RNA. Post-transfection incubation between 6 hr and overnight did not significantly affect CAT activity.

For translation of RNAs in poliovirus infected cells, HUH7 cells were infected with Poliovirus (Mahoney strain, ATCC VR-59) at a multiplicity of infection (MOI) of 100. Cells were transfected with RNAs 2 hr after the infection and were harvested 4 hr after the transfection. Cells maintained normal morphology during the 6 hr infection, after which they began to change morphology and detach from the culture dish.

G. Transfection of dicistronic DNA constructs into cells. Twenty micrograms of each plasmid DNA purified by banding in a CsCl gradient were transfected into $2 \times 10^6$ HUH7 cells.by calcium phosphate method (Gorman et al.). The cells were harvested 48 hr after transfection and cell extract was prepared by repeated freezing and thawing. The CAT assay was performed as described (Gorman et al.). The LacZ assay was according to Miller (Miller, Assay of beta-galactosidase. In "Experiments in Molecular Genetics", pp. 352–355, Cold Spring Harbour Laboratory, Cold Spring Harbour, N.Y., 1972).

Example 1

Construction of RNAs with Deletions in the 5'UT Region of the HCV Genome and Rationale for the Method.

In order to map cis-acting element(s) controlling translation in the HCV genome, full-length (from nucleotide 1 to 341) or deleted versions of the 5'UT region of HCV-1 RNA were linked to the coding region of chloramphenicol acetyl transferase (CAT) mRNA. The constructions are illustrated in FIG. 3 and described in Table 1, below.

TABLE 1

| Construct ID | Seq. of 5' UT Region | Delection or Other Feature |
|---|---|---|
| R1 | 1–341 | |
| R2 | 23–341 | 1–22 deleted |
| R3 | 35–341 | 1–34 deleted |
| R4 | 83–341 | 1–82 deleted |
| R5 | 99–341 | 1–98 deleted |
| R6 | 145–341 | 1–144 deleted |
| R6.hp | 145–341 | 1–144 deleted with hairpin bases 1–23 added at 5' end 1–23 added |
| R7 | 218–341 | 1–217 deleted |
| R8 | 255–341 | 1–254 deleted |
| R8.hp | 255–341 | 1–254 deleted with hairpin bases 1–23 added at 5' end |
| R9 | 322–341 | 1–321 deleted |
| R11 | 1–322 | 323–341 deleted |
| R13 | 1–205 | 206–341 deleted |
| R14 | 1–145 | 146–341 deleted |
| R17 | 145–322 | 1–144 and 323–341 deleted |
| R18 | 145–294 | 1–144 and 295–341 deleted |

Each RNA was synthesized by transcribing a DNA fragment with T7 polymerase, which was first amplified by PCR to contain a specific 5' or 3' deletion. Each RNA was designed to have a cap at the 5' end and a poly A tail (A40) at the 3' end to increase stability in cells. This approach allows an efficient production of a large amount of RNA with unifornrly defined 5' and 3' ends. Unlike conventional DNA transfection strategies, RNA transfection of cells using this approach circumvents possible splicing and transport problems that certain RNA molecules may encounter in the nucleus.

By the same method, two additional RNAs were synthesized: 1) the SVCAT with the 5' leader of SV40 early mRNA that served as a positive control for a conventional cap-dependent translation (Kozak, "The scanning model for translation: An update," *J. Cell Biol.* (1989) 108:229–241), and the EMCVCAT with the 5' leader of EMCV that served as a positive control for cap-independent internal initiation (Jang et al., "Initiation of protein synthesis by internal entry of ribosomes into the 5' nontranslated region of Encephalomyocardits virus RNA In vivo," *J. Virol.* (1989) 63:1651–1660).

Example 2

Translation of Hybrid CAT RNAs in vitro.

In order to confirm that synthetic RNAs were biologically active and to determine their translational profile in vitro, the RNAs of Example 1 were translated in rabbit reticulocyte lysate. All RNAs including SVCAT generated a CAT protein of the expected size.

The in vitro results can be summarized as follows: 1) In HCVCAT constructs, R1 to R5 produced CAT protein, but only at barely detectable levels. This level of translation gradually increased in R6 and in R7, reaching a maximum 12-fold increase in R8. 2) At KC1 concentration of 140 mM the in vitro translation of capped SVCAT and HCVCAT RNAs (R7, R8) was more efficient than that of the uncapped RNAs by an average of 20-fold. 3) At lower KC1 concentrations (50 to 100 mM), translation of uncapped R1 template generated CAT protein at levels comparable to that of the capped R1 template, possibly indicating the occurrence of weak internal initiation.

Surprisingly and unexpectedly, these results are contrary to recent data by Tsukiyama-Kohara et al. "Internal ribosome entry site within hepatitis C virus RNA," *J. Virol.* (1992) 66:1476–1483, who reported the detection of an internal ribosome entry site within the 5'UT region of HCV RNA using rabbit reticulocyte lysate and HeLa cell extracts. Protein synthesis in vitro using cell lysates does not always faithfiully represent translation conditions in vivo (Kozak, "Comparison of initiation of protein synthesis in prokaryotes, eukaryotes, and organells," *Microbiol. Rev.* (1983) 47:1–45). An alternate approach was used.

Example 3

Translation of Hybrid CAT RNAs in vivo and Identification of Control Elements.

In order to determine the translation profile of the monocistronic constructs in vivo, RNAs were transfected (R1 to R18) along with the control RNA, SVCAT, into a human hepatocyte cell line (HUH7) using lipofectin (Felgner et al.). CAT activities were monitored, and the data summarized in Table 2.

TABLE 2

| Construct ID | Seq. of 5' UT Region | Deletion or Other Feature | CAT Activity |
|---|---|---|---|
| R1 | 1–341 | | undetected |
| R2 | 23–341 | 1–22 deleted | 0.5 |
| R3 | 35–341 | 1–34 deleted | 2.0 |
| R4 | 83–341 | 1–82 deleted | 2.1 |
| R5 | 99–341 | 1–98 deleted | 2.5 |
| R6 | 145–341 | 1–144 deleted | 2.1 |
| R6.hp | 145–341 | 1–144 deleted with hairpin bases 1–23 added at 5' end | 0.1 |
| R7 | 218–341 | 1–217 deleted | 5.2 |
| R8 | 255–341 | 1–254 deleted | 7.9 |
| R8.hp | 255–341 | 1–254 deleted with hairpin bases 1–23 added at 5' end | 0.1 |
| R9 | 322–341 | 1–321 deleted | 0.6 |
| R11 | 1–322 | 323–341 deleted | undetected |
| R13 | 1–205 | 206–341 deleted | undetected |
| R14 | 1–145 | 146–341 deleted | undetected |
| R17 | 145–322 | 1–144 and 323–341 deleted | 1.5 |
| R18 | 145–294 | 1–144 and 295–341 deleted | 0.6 |

In the full-length construct R1, CAT activity was repeatedly undetectable unless the amount of RNA was increased by 10-fold and more cell extract was used. This result suggested that the full-length HCV RNA may not be an efficient translation template in vivo.

A series of 5' deletion constructs as described in Example 1 were analysed. CAT activity was first detected in R2 in which the 5' terminal hairpin of 23 nucleotides was removed. This activity increased by 4-fold in R3 and a similar level of activity was detected in R4, R5 and R6, which were systematically deleted for ORF 1 to 4.

The 5'UT sequence in R6 was identical to that of the 5' subgenomic RNA detected in vivo (Ran et al., 1991). The CAT activity further increased by 2-fold in R7 in which the AUG codon of ORF 5 was removed and an additional 1.5-fold in R8 which retains only 86 nucleotides of 3' proximal sequence. The construct R8 represents maximum CAT activity. These data suggest that sequences upstream from nucleotide 255 including the small ORFs are inhibitory to the translation from the major initiation codon for the polyprotein.

The maximum CAT activity seen in R8 decreased sharply upon a further deletion of 67 nucleotides in the R9 construct. This result suggests that an efficient positive control element that stimulates translation may be present downstream from nucleotide 255. This 86 nucleotide region contains a 28 nucleotide sequence with 90% identity to pestiviruses and is referred to as the pestivirus homology box IV, designated in FIGS. 2 and 3 as PEST-IV (Han et al., 1991). To determine whether the PEST-IV element is solely responsible for the observed translation stimulation, the RNA construct R6 was subjected to deletion analysis.

The construct R6 has a deletion of sequence 1–145 of the 5'UT region removing the portion of the 5' terminus of HCV RNA associated with inactive constructs. R6 was favored for deletion analysis over R8. A 3' deletion in R8 would generate RNA with a short 5'UT region.

Upon transfection, the CAT activity seen in R6 was reduced 1.5-fold by a deletion of 20 nucleotides from the 3' end of R6, in the construct R17 and a further 2.5-fold decrease by an additional deletion of 28 nucleotides, in the construct R18.

These data indicated that additional upstrean and downstream sequences from the PEST-IV were necessary for maximum translational enhancement. The PEST-IV sequence appears to be a part of a positive cis-acting element which can be transferred to a heterologous 5' leader. Turning now to FIG. 4, this 28 base sequence was inserted into the SVCAT to create SV*CAT and conferred an increase in CAT activity of 3-fold.

Other RNA constructs were made with 3' deletions. No CAT activity was detected in R11 and R14 as well as in R13, all of which contained the 5' hairpin. These data are consistent with the view that the 5' hairpin is inhibitory to the translation of HCV RNA.

Example 4

The Effect of 5' Hairpin of HCV on the Translation of CAT RNAs.

Since RNAs with the intact 5' terminus were all inactive irrespective of the downstream sequences, a potential 5' hairpin structure resident in the most distal 23 nucleotides was evaluated with respect to the observed translation inhibition. Accordingly, the 5' hairpin was linked to the 5' terminus of the two active RNAs, R6 and R8. These RNAs, R6hp, R8hp, were transfected into HUH7 cells and the CAT activity was measured.

Returning to Table 2, the juxtaposition of the hairpin on these constructs nearly abolished the translation as demonstrated by the relative CAT activity. The data suggest that the 5' hairpin is a potent translation inhibitor, although complete inhibition requires more nucleotides than the 23 nucleotide hairpin alone.

Example 5

Translation of Hybrid CAT RNAs in Poliovirus-infected Cells.

Poliovirus infection is known to inhibit the cap-dependent translation of cellular RNA and thereby promote translation of its own or heterologous RNA which contains an internal ribosome entry site (IRES) within its 5' UT region (Jang et al., "Initiation of protein synthesis by internal entry of ribosomes into the 5' nontranslated region of Encephalomyocarditis virus RNA in vivo," J. Virol. (1989) 63:1651–1660; Macejak and Sarnow, "Internal initiation of translation mediated by the 5' leader of a cellular RNA," Nature (1991) 353:90–94; Pelletier and Sonenberg, "Internal initiation of translation of eukaryotic mRNA directed by a sequence derived from poliovirus RNA," Nature (1988) 334:320–325). This inhibition is believed to be mediated indirectly by the poliovirus encoded proteinase 2A, by activating an unidentified latent cellular protease which in turn cleaves p220, a component of the cellular cap-binding protein complex (e1F–4F) (Soneneberg, "Cap-binding protein of eukaryotic mRNA: functions in initiation and control of translation," Prog. Nucleic Acid Res. Molec. Biol. (1988) 35:173–297).

Hybrid CAT RNAs with various 5'UT regions were transfected into HUH7 cells infected with poliovirus. This strategy was designed to determine the cap dependency of each RNA and to detect the possible existence of a weak internal ribosome entry site (IRES) which may be present in the HCV 5' UT region.

As expected, poliovirus infection increased CAT activity by 7-fold in EMCVCAT over a positive control RNA for internal initiation (Elroy-Stein et al.). In contrast, the polio infection substantially decreased CAT activity in SVCAT as well as in two HCV constructs, R6 and R8, respectively. The lowered CAT activities seen in poliovirus infected cells were further diminished if infected cells were incubated longer (2.5 hrs) prior to RNA transfection. The CAT activity of R1 remained undetectable regardless of poliovirus infection. This result strongly suggests that an IRES is not present in the 5'UT region of HCV RNA.

With the exception of the R1 construct, the constructs tested in the above experiment contained large deletions of the 5'UT region. It is possible that such deletions may have affected a putative IRES structure and/or function. To evaluate the effect of such deletions, constructs with less extensive deletions were tested for their ability to translate CAT protein in poliovirus infected cells. In agreement with the previous results, the CAT activity of the R1 construct remained undetectable in the presence or absence of poliovirus infection. Constructs R2 to R5 showed relative levels of CAT activity similar to those described previously when tested in the absence of poliovirus infection. However, the CAT activities of the HCV leader templates were practically abolished in the poliovirus infected cells.

In addition, templates SVCAT and R1 to R3 were tested in a similar protocol using uncapped messages. The uncapped templates were inactive in transfected cells whether or not the cells were subsequently infected with poliovirus. These results strongly suggest that monocistronic messages with cis-acting regulatory elements derived from the HCV 5'UT region are translated by a cap-dependent mechanism and that the HCV 5'-noncoding region does not have an IRES element.

Example 6

Translation of Dicistronic mRNA in HUH7 Cells.

Figure 5:
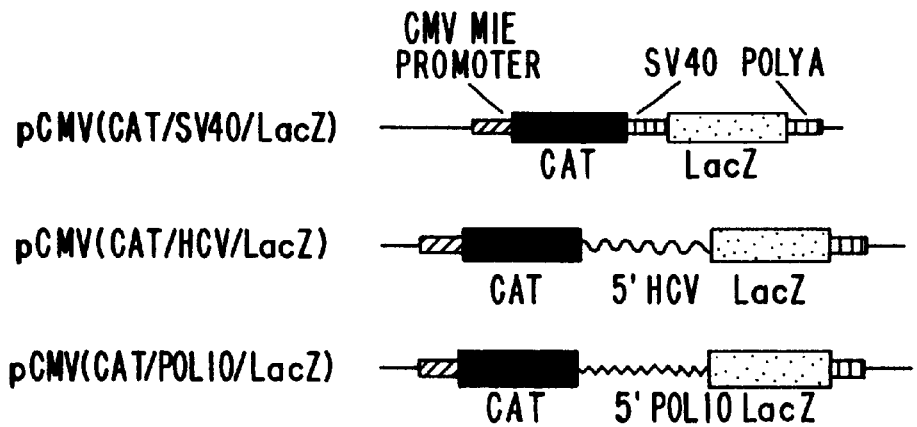
FIG. 5 is a schematic representation of three RNA constructs, pCMV (CAT/SV40/LacZ), pCMV (CAT/HCV/LacZ) and pCMV (CAT/polio/LacZ)

The possible presence of an IRES within the 5'UT region of HCV was further tested by transfecting HUH7 cells with DNA constructs designed to transcribe a dicistronic mRNA. Thus the 5'UT region of HCV RNA was placed as an intercistronic spacer between CAT as the first cistron and LacZ as the second cistron. The linked DNA was cloned into an expression vector, in which transcription is driven by the strong enhancer-promoter of the major immediate early gene in cytomegalovirus (CMV). Positive and negative control dicistronic vectors, in which the 5'UT region of HCV was replaced with the 5'UT region of poliovirus and the 3'UT region of SV40 early gene were constructed as depicted in FIG. 5.

Figure 6:
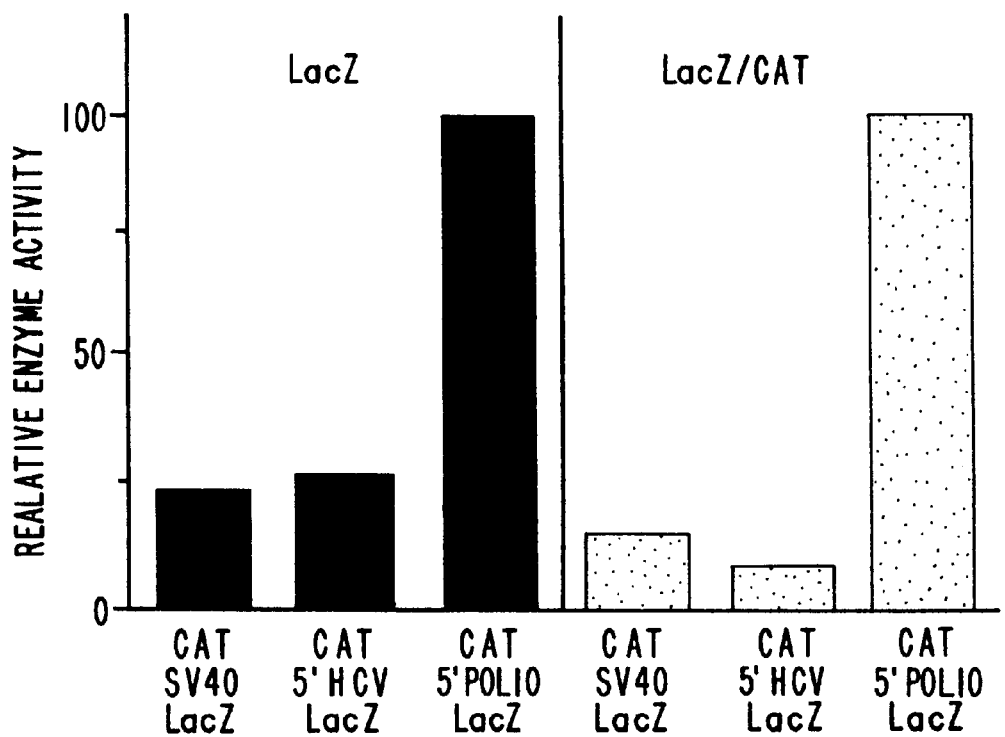
FIG. 6 graphically depicts activity of the LacZ and LacZ/CAT constructs of FIG. 5.

Upon transfection into HUH7 cells, all three constructs supported translation of the first CAT cistron at a comparable level. Turning now to FIG. 6, the enzyme activities of the three constructs are summarized in bar graph form. The dicistronic construct with the HCV leader did not support the translation of the second LacZ cistron at a level comparable to the dicistronic control construct employing a poliovirus leader. These data support the earlier evidence generated using monocistronic constructs that the full-length 5'UT region of HCV genome does not contain an IRES.

Example 7
Translation of HCV RNA Constructs in HeLa and HepG2 Cells.

Transient transfection assays can give different readouts that are cell line dependent. In order to ensure that the results obtained were not confined to HUH7 cells, R1, R7 and R8 constructs were transfected into HeLa and HepG2 cells. The resultant patterns of CAT activity were qualitatively similar to that observed in HUH7 cells.

Example 8
The Control of the Control Elements of the 5'UT Region of HCV with Antisense Molecules.

Methods of making oligonucleotide analogs and derivatives and their use as antiviral agents are reported in, inter alia; PCT WO88/07544 and PCT WO91/16331.

Sulfurized oligonucleotide analogs are prepared for use as antisense agents in accordance with the teachings of PCT WO91/16331. A 23 base phosphorothioate oligonucleotide corresponding to the antisense of bases 1–23 of (SEQ ID NO: 1) is synthesized by the phosphoramidite method on an automated synthesizer (model 380B Applied Biosystems, Foster City, Calif.). The standard synthesis protocol is followed, except that in the place of the oxidation step, a sulfurization step is substituted, which sulfurization step precedes the capping step. Thus, the synthesis consists of repeated cycles of detritylation, coupling, sulfurization, and capping. Separation of the final product from the synthesis column and purification is accomplished by standard means.

The sulfurization step is performed by exposing the growing chain to a 0.2 M solution of O,O-diisopropylphosphorodithioic acid disulfide in pyridine for one minute at room temperature. The yield of trityl cation released during the detritylation steps is anticipated to average 99%. The trityl yield is both a measure of coupling efficiency and a measure of the sulfurization, since nonsulfurized or oxidized trivalent phosphorous linkages in the oligonucleotide are labile to cleavage during detritlation.

The 23 mer corresponding to the antisense of bases 1–23 of (SEQ ID NO: 1) is cleaved from the support and deprotected with concentrated ammonium hydroxide at 55° C. for 6 hours. The tritylated oligonucleotide is isolated by HPLC, detritylated, and precipitated as sodium salt. The phosphorothioate analog is resistant to nucleases normally present in cells.

It is anticipated that cells cultured with concentrations of the phosphorothioate oligomer would be resistant to HCV viral infection at concentrations as low as 0.5 mM.

It is anticipated that the 23mer oligonucleotide analog complementary to Sequences 1–23 of the sense RNA, decreases the translation of HCV messenger RNA by binding to and stabilizing the hairpin configuration.

Example 9
Control of the 5'UT Region Using an Anti-hairpin Molecule

This example utilizes a 28 nucleotide sequence corresponding to the sequences of pestivirus homology box IV. In accordance with International Patent Application No. PCT WO88/07544, a phosphorothioate oligonucleotide analog complementary to bases 291 through 318 of (SEQ ID NO: 1) is synthesized.

The phosphorothioates of the present invention are synthesized in an Applied Biosystems 380-B DNA Synthesizer in a manner similar to that of the synthesis cycle for normal phosphate oligonucleotides using O-methylphosphoramidite. The major difference is in the reagents used during the oxidation step.

A 5% sulfur solution consisting of 7.5 grams of $S_8$ elemental sulfur, dissolved first in 71 ml carbon disulfide along with 71 ml pyridine and 7.5 ml triethylamine, is used as the oxidizing reagent. The total volume given is sufficient for a 3 column synthesis of a 30 mer.

Before and after the oxidation step, the column is washed repeatedly with a 1:1 solution of carbon disulfide and pyridine to remove any residual sulfur which might precipitate in the lines. For a three column synthesis of a 30 mer, a total volume of 380 ml of this solution should be sufficient. The solutions should be as anhydrous as possible, and should be remade for each new synthesis.

The sulfur oxidation is not as rapid as iodine oxidation, and thus requires a waiting step of 450 seconds during the synthesis cycle, as compared to 30 seconds for the iodine oxidation waiting step. Additionally, the end procedure is slightly altered in that the reverse flush is held five seconds longer than normal for a total of ten seconds to ensure the removal of any resulting salts dissolved in methanol after thiophenol is delivered to the column.

The 28 nucleotide phosphorothioate nucleic acid analog is synthesized by automatically changing the oxidation cycle at the required point. After cleavage from the column and deblocking in aqueous ammonia (60°, 10 h), phosphorothioate oligomers and block copolymers are purified via reverse phase HPLC (PRP-1 column, 1% triethylammonium acetate buffer, pH 7-acetonitrile (20%, increase to 40% at 20 minutes), and the solution is extracted with two equal volumes of ethyl acetate, frozen in dry ice, and lyophilized.

The solids are dissolved in 0.3 ml of 1M NaCl, and the product is precipitated by the addition of 3.5 volumes of absolute ethanol. The acetate salts of some phosphorothioate oligomers, particularly the homopolymer $dC_{28}$, are extremely insoluble in 1M NaCl. Introduction of a small amount of ammonia vapor (not aqueous ammonia), by a Pasteur pipette solubilizes all the solids.

Cells brought into contact with solutions containing 0.5 mM concentrations of the 28 nucleotide analog are anticipated to exhibit resistance to the HCV infection or HCV expression of viral proteins.

Example 10
Control of the 5'UT Region Using AS5 Antisense Molecules

A 24-mer antisense oligonucleotide designated AS5, which binds to nucleotides 277–300 of the 5' UT region of HCV region was synthesized as above with the following sequence: 5'CCTATCAGGCAGTACCACAAGGCC 3' (SEQ. ID NO: 2)

AS5-PO designates the AS5 oligonucleotide having normal phosphodiester linkages. AS5-PS designates the AS5 oligonucleotide wherein all the internucleoside linkages are phosphorothioate linkages, and is synthesized as in Example 9 above. AS5-3' CHOL-PS and AS5-3' CHOL-PO designate the AS5-PS and -PO oligonucleotides respectively, wherein a cholesteryl group is added to the 3' end of the molecule, and were synthesized by Lynx Pharmaceuticals (Foster City, Calif.). The cholesteryl group may also be added to the 3' end by methods described herein.

The antisense oligonucleotides (ASOs) were tested in the following assay to determine their ability to inhibit translation controlled by the 5' UT region of HCV. HUH-7 cells were grown as described in Materials and Methods. Various antisense molecules (AS5-PO, AS5-PS, AS5-3' CHOL-PS, and a control 21-mer sequence derived from herpes simplex virus (HSV) in —PO, —PS and 3'-CHOL embodiments) were supplemented to the HUH-7 cell culture medium at varying final concentrations of 0.1 to 1.0 μM and incubated for 12–24 hours.

Figure 7:
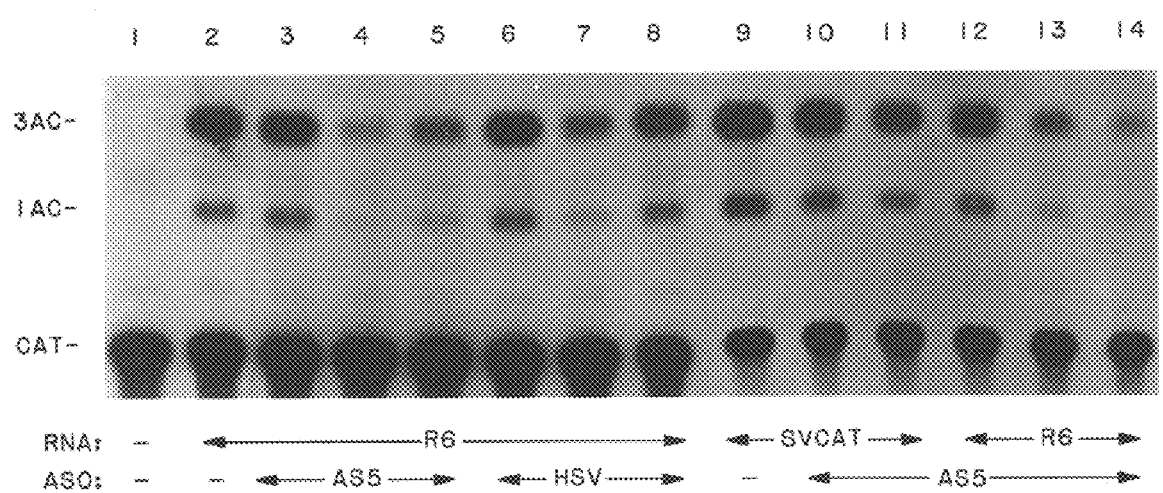
FIG. 7 shows the results of the effects of AS5 antisense molecules on R6 transcription.

After incubation with the ASO, cells were then transfected with test RNAs (R6 and SVCAT RNA as described in Example 5 and FIGS. 2 and 3) as follows: 2 to 4 μg of each RNA were mixed with 15 μg of Lipofectin (Gibco-BRL) in 200 μl of phosphate buffered saline, incubated for 15 minutes and added to the cells as described in Section F of Materials and Methods, above. CAT activity was assayed as in Section F above (C. M. Gorman et al., *Mol. Cell. Biol.* (1982) 2:1044–1051). The results are displayed in FIG. 7.

Columns 2 and 11–13 contain SVCAT template RNA, while columns 3–9 and 14–18 contain R6 template RNA. Columns 1–3, 10–11 and 14 are controls with no ASO incubation. The remaining columns contain AS5 or HSV control ASOs as indicated. The data show that the AS5-3' CHOL-PO and AS5-3' CHOL-PS ASOs specifically inhibit CAT transcription and translation under control of the HCV 5' UT region, and do not inhibit such transcription and translation under control of the SV40 promoter region.

The foregoing description of the specific embodiments will so fully reveal the general nature of the invention that others can, by applying current knowledge, readily modify and/or adapt for various applications such specific embodiments without departing from the general concept, and therefore such adaptations and modifications are intended to be comprehended within the meaning and range of equivalents of the disclosed embodiment.

We claim:

1. A method of enhancing the translation of a coding region comprising the steps of:

making an RNA molecule comprising the coding region and a 5' untranslated region operably linked to said coding region, said 5' untranslated region comprising a sequence fully homologous to a sequence of the pestivirus homology box IV; and translating the RNA molecule, wherein the translation of the coding region is enhanced.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (C) INDIVIDUAL ISOLATE: ns5hcv1

(xi) SEQUENCE DESCRIPTION: SEQ ID NO:1:

```
GCCAGCCCCC TGATGGGGGC GACACTCCAC CATGAATCAC TCCCCTGTGA GGAACTACTG        60

TCTTCACGCA GAAAGCGTCT AGCCATGGCG TTAGTATGAG TGTCGTGCAG CCTCCAGGAC       120

CCCCCCTCCC GGGAGAGCCA TAGTGGTCTG CGGAACCGGT GAGTACACCG GAATTGCCAG       180

GACGACCGGG TCCTTTCTTG GATCAACCCG CTCAATGCCT GGAGATTTGG GCGTGCCCCC       240

GCAAGACTGC TAGCCGAGTA GTGTTGGGTC GCGAAAGGCC TTGTGGTACT GCCTGATAGG       300

GTGCTTGCGA GTGCCCCGGG AGGTCTCGTA GACCGTGCAC C                          341
```

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA -continued (iii) HYPOTHETICAL: NO (iv) ANTI-SENSE: YES (xi) SEQUENCE DESCRIPTION: SEQ ID NO:2:

CCTATCAGGC AGTACCACAA GGCC                                              24

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

TAATACGACT CACTATAG                                                     18

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

TTTTTTTTTT TTTTTTTTTT TTTTTTTTTT TTTTTTTTTT                              40

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

GGAGGAGTAG                                                              10